United States Patent [19]

Kleemann et al.

[11] Patent Number: 4,562,152

[45] Date of Patent: Dec. 31, 1985

[54] PROCESS FOR OBTAINING PURE L-LEUCINE

[75] Inventors: Axel Kleemann, Hanau; Jürgen Martens, Alzenau; Horst Weigel, Rodenbach, all of Fed. Rep. of Germany

[73] Assignee: Degussa Aktiengesellschaft, Frankfurt, Fed. Rep. of Germany

[21] Appl. No.: 612,802

[22] Filed: May 22, 1984

[30] Foreign Application Priority Data

May 25, 1983 [DE] Fed. Rep. of Germany ....... 3318932

[51] Int. Cl.$^4$ ..................... C12P 13/06; C07P 41/00
[52] U.S. Cl. .................................... 435/116; 435/280
[58] Field of Search ................................ 435/116, 280

[56] References Cited

U.S. PATENT DOCUMENTS 3,841,966 10/1974 Soichiro et al. ................. 435/280
4,259,441 3/1981 Bauer ............................. 435/116

*Primary Examiner*—Lionel M. Shapiro
*Attorney, Agent, or Firm*—Cushman, Darby & Cushman

[57] ABSTRACT

Pure L-leucine is obtained from an aminoacid mixture which contains at least 45 weight percent L-leucine, at most 40 weight percent L-isoleucine and at most 25 weight percent of other aminoacids by acetylating the mixture, precipitating the acetylation product by acidification, subjecting the acetylation product to a saponification by an L-aminoacid acylate until 30 to 95% of the N-acetyl-L-leucine employed is saponified and isolating the L-leucine from the saponification mixture.

8 Claims, No Drawings

PROCESS FOR OBTAINING PURE L-LEUCINE

BACKGROUND OF THE INVENTION

The invention is directed to a process for obtaining pure L-leucine from an aminoacid (aminocarboxylic acid) mixture which contains at least 45 weight percent L-leucine, at most 40 weight percent L-isoleucine and at most 25 weight percent of other aminoacids, in each case based on the dry material.

L-leucine is employed as a pharmaceutical, e.g. as a component of infusion solutions based on aminoacids. Until now the industrial manner of obtaining L-leucine is the so-called extraction process. For this purpose proteins are hydrolyzed to aminoacid mixtures and an industrial L-leucine is obtained from this by fractional crystallization and/or a chromatographic process (ion exchange, ion exclusion and/or the molecular sieve effect).

The thus obtained technical leucine contains in addition to inorganic salts such as sodium chloride, sodium sulfate, ammonium chloride or ammonium sulfate other aminoacids, especially L-isoleucine. To produce L-leucine in pharmaceutical quality there must be removed these impurities, whereby especially the separation of L-isoleucine causes difficulties since isoleucine has the same empirical formula $C_6H_{13}NO_2$ as leucine and the two aminoacids differ only in the structure of the aliphatic side chain.

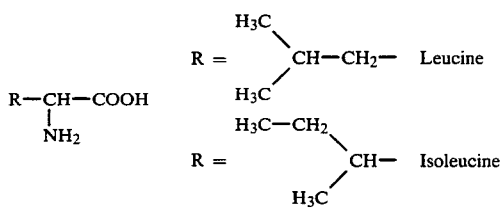

Based on the very similar structural characteristics these aminoacids exhibit very similar properties in their physical and chemical behavior. This is also the reason why commercial L-leucine frequently contains significant amounts of L-isoleucine in addition to other aminoacids (e.g. L-valine, frequently also L-methionine). In regard to these conditions see also Richard J. Block [Arch. Biochem. Vol. 11, 501 (1946), page 512].

The difficult purification of industrial L-leucine has already been realized via the copper complex. In a similar process the cobalt complexes of the aminoacids were also separated by extraction with alcohol. However, in this process there is the problem of the recovery of the metal and the further purification of the L-leucine.

Other authors have described the precipitation of leucine with aromatic sulfonic acids. Thus there has been proposed the use of 2-bromotoluene-5-sulfonic acid or naphthalene-2-sulfonic acid for the precipitation of L-leucine. Also benzenesulfonic acid and p-toluenesulfonic acid have been employed for obtaining L-leucine starting from industrial L-leucine. In this process the precipitate must be purified by numerous recrystallizations and the separation of the frequently very toxic precipitation agent causes an additional problem.

Furthermore fractions of the acid protein hydrolysates rich in L-leucine have been purified by establishing an L-isoleucine concentration of about 1.5% with addition of water at a specific pH and after ascertaining the methionine content oxidizing the methionine by addition of hydrogen peroxide. Clarification with activated carbon is carried out, adjustment of the pH to 1.0 to 1.5, cooling and separation of a crude L-leucine. This is dissolved again at pH 0.5 and again purified by precipitation at pH 1.0 to 2.0. This process is repeated frequently until the desired purity of L-leucine is attained. The process which is described in European patent 14867 requires working with very dilute materials and besides the process requires so many steps that it scarcely can be considered for use on an industrial scale.

Furthermore the known processes for the purification of industrial L-leucine to obtain pure L-leucine in pharmaceutical quality have a decisive fault. Nothing is said in regard to the purity of the enantiomer of the L-leucine. Leucine, however, is among the quickest racemizing aminoacids under the conditions of the customary acid hydrolysis of protein (Liebig's Ann. Chem 1981, pages 354 to 365).

The different biological effect of D-leucine and L-leucine is known so that a process which simultaneously permits the separation from D-leucine and from other impurities present in industrial L-leucine is very much desired.

SUMMARY OF THE INVENTION

The process of the invention comprises:

(a) acetylating the aminoacid mixture (i.e. the aminocarboxylic acid mixture) in known manner, (b) precipitating a mixture of N-acetylaminoacids enriched in N-acetyl-L-leucine from the crude mixture of acetylation products by acidifying with a mineral acid, (c) subjecting this N-acetyl-L-leucine enriched mixture in aqueous solution having concentration between 0.1 and 1.5 moles/l of N-acetyl-L-leucine at a pH between 6 and 8 and a temperature between 10° and 40° C. in the presence of an effector of saponification by a L-aminoacid acylase until 30 to 95% of the N-acetyl-L-leucine is hydrolyzed to the free aminoacid, and (d) isolating L-leucine from the crude hydrolysis mixture.

As starting aminoacid mixtures for the process of the invention there are generally employed industrial L-leucine in the form of a fraction from a protein hydrolysate which fraction is already enriched in L-leucine. Especially suited are aminoacid mixtures which, based on dry material, contain 45 to 90 weight percent L-leucine. An especially suitable industrial L-leucine originates from the fractionation of blood meal hydrolysate and contains 70 to 80 weight percent L-leucine, 5 to 15 weight percent L-isoleucine and a maximum of 35 weight percent of other aminoacids.

The aminoacid mixture is first acetylated in known manner. The acetylation can be carried out with acetyl chloride or acetic anhydride or even with ketene according to the process known from German OS No. 2741081.

Subsequently a mixture of N-acetylaminoacids is precipitated from the crude mixture of acetylation products by acidification with a mineral acid, e.g. hydrochloric acid or sulfuric acid. Thereby suitably it is acidified to a pH between 0.5 and 2. Thereby there already occurs an enrichment of N-acetyl-L-leucine. The content of N-acetylaminoacids other than N-acetyl-L-leucine and N-acetyl-L-isoleucine which may be present is reduced. Through a subsequent recrystallization from water, an aliphatic alcohol having 1 to 4 carbon atoms and miscible with water, such as methanol, ethanol, n-propanol, isopropyl alcohol, n-butanol, isobutyl alcohol or t-butyl alcohol or a mixture of water and such an alcohol, there can normally be reduced the content of other N-acetyl-aminoacids to less than 4, in many cases to less than 1 weight percent based on the dried material.

The mixture enriched in N-acetyl-L-leucine which after a possible recrystallization is almost only contaminated by N-acetyl-L-isoleucine is than subjected to a saponification by an L-aminoacid acylase. The adjustment of the pH to the range between 6 and 8 for example, can be carried out with ammonia, but preferably there is used sodium hydroxide liquor. As effectors, there can be added those customarily added in the resolution of N-acetyl-DL-α-amino-carboxylic acids by means of an L-aminoacid acylase, for example, the ions $Ca^{2+}$, $Fe^{2+}$, $Mn^{2+}$, $Mg^{2+}$, $Zn^{2+}$, and preferably $Co^{+2}$. They are suitably employed in a concentration between $1 \times 10^{-5}$ and $1 \times 10^{-1}$ moles/l and for example, in the form of the corresponding chloride. In many cases it is advantageous to add to the reaction mixture additional small amounts of a biocide, for example p-hydroxybenzoic acid n-propyl ester.

As L-aminoacid acylase there is preferably employed a renal acylase. It can be used either in the commercial native form or as an immobilizate on organic carriers such as cross-linked agarose, dextran gels, cellulose, hydroxyethyl cellulose or mixed polymerizates of acrylamide with cross-linking comonomers, or on inorganic carrier materials such as various porous oxidic materials or especially glass beads.

The reaction time needed for the hydrolysis can be shortened by using a relatively large amount of L-aminoacid acylase. Making allowance for longer reaction times the amount of L-aminoacid acylase added can be reduced considerably. Accordingly there is a marked relationship between the reaction time and the amount of L-aminoacid acylase employed.

The hydrolysis, thus reaction step (c) is broken off when 30 to 95%, preferably 45 to 85%, especially 50 to 80% of the N-acetyl-L-leucine originally present is hydrolyzed to the free L-leucine. The hydrolysis reaction is followed analytically, e.g. by means of a high pressure liquid chromatography or with an aminoacid analyzer.

The hydrolysis reaction can be carried out discontinuously or continuously. For the discontinuous reaction, the process is carried out with a stirring kettle or in a tank with recirculation. A continuous reaction is carried out for example by means of an enzyme-membrane reactor.

If the mixture employed for the hydrolysis reaction has a relatively high concentration of N-acetyl-L-leucine, for example, between 1.0 and 1.5 moles/l then after a short time, there begins to crystallize out a colorless precipitate, which precipitate consists of pure L-leucine. If the mixture is employed in lower concentrations, it is suitable to concentrate the crude hydrolysis mixture under careful conditions, in which case pure L-leucine also crystallizes out. In both cases, the pure L-leucine is isolated by filtering off or centrifuging, in a given case, after previous classification for the purpose of separating off a immobilized L-aminoacid acylase which may have been employed.

If the hydrolysis is carried out with native L-aminoacid acylase, then after the separation off of the L-leucine by ultra-filtration the L-aminoacid acylase can be recovered, e.g. on a hollow fiber membrane, and employed again.

It can be advantageous in some circumstances to isolate the L-leucine in several fractions, i.e. after separation of a first fraction continuing the hydrolysis and obtaining further fractions of L-leucine. A further purification of individual fractions or of the entire amount of separated off L-leucine which is desirable in a given case, can be carried out by recrystallization from water.

The N-acetyl-L-isoleucine is noticeably enriched in the solution remaining after separation of the L-leucine and in a given case, of the L-aminoacid acylase. This solution, suitably after determination of its composition by high pressure liquid chromatography or with an aminoacid analyzer can either be returned to the acelylation step or be worked up to L-isoleucine.

The invention is further explained in the following examples. The following applies to these examples:

The activity of the L-aminoacid acylase is given in units (U). 1 U at a pH of 7.0 and 25° C. hydrolyzes 1μ mole of N-acetyl-L-methionine per hour.

The rotary value $[\alpha]_D^{25}$ given for the L-leucine was measured at c=4 in 6N hydrochloric acid. The rotary value of the pure L-leucine in pharmaceutical quality according to the U.S. Pharmacopoeia XX under these conditions is L-Leucine $[\alpha]_D^{25} = +14.9°$ to $+17.3°$ The determination of the composition of the starting mixture of aminoacids employed is carried out with an aminoacid analyzer.

Unless otherwise indicated, all parts and percentages are by weight.

The process can comprise, consist essentially of, or consist of the recited steps with the stated materials.

EXAMPLE 1

There was acelylated an industrial leucine of the following relative aminoacid composition and obtained as a byproduct in the hydrolysis of soybeans.

| | |
|---|---|
| Ile | 12.4% |
| Leu | 83.2% |
| Val | 0.9% |
| Met | 2.4% |
| Ala | 0.5% |
| Ser | 0.2% |
| Other amino acids | collectively 0.4% |

For this purpose 525 grams of this mixture were dissolved in 2 liters of 2N aqueous sodium hydroxide and at 0° C. within 1 hour there were added dropwise 450 ml of acetic anhydride and 850 ml of 5N of aqueous sodium hydroxide, whereby attention was paid that the pH remained in the region between 10 and 12 and the temperature did not exceed +5° C. The brown solution was stirred with concentrated hydrochloric acid until there was reached pH 1. By filtering with suction, washing with water and drying there were obtained 580 grams of solid material. This crude product was recrystallized from aqueous methanol whereby there were obtained 435 grams of a colorless mixture of 90% N-acetyl-L-leucine and 10% N-acetyl-L-isoleucine.

86.6 grams of this mixture were dissolved in 1 liter of 0.5N aqueous sodium hydroxide and the pH was adjusted to 7.4. As catalyst there was added 40 mg of renal acylase from pig kidneys (1200 U/mg) and 60 mg of $CoCl_2 \times 6H_2O$. The clear solution was heated to 39° C. After 2¾ hours the first crystals formed. After 10 hours the mixture was cooled to 20° C. and the voluminous precipitate was filtered off with suction and washed with water.

After drying there were obtained 35.6 grams of pure L-leucine having a rotary value of $[\alpha]_D^{25} = +15.3°$.

The filtrate was stationary for 24 hours at 20° C. whereby crystals separated off anew. After filtering with suction, washing with water and drying there were obtained an additional 9.3 grams of pure L-leucine having a rotary value $[\alpha]_D^{25} = +16.2°$.

EXAMPLE 2

A fraction of neutral aminocarboxylic acids which was obtained by chromatographic separation of a protein hydrolysate had the following composition:

| | | |
|---|---|---|
| | Leu | 49.8% |
| | Ile | 36.1% |
| | Val | 3.5% |
| | Met | 3.5% |
| | Tyr | 2.5% |
| | Ala | 2.1% |
| | Phe | 1.6% |
| | Gly | 0.9% |

525 grams of this mixture were dissolved in 2 liters of 2N aqueous sodium hydroxide and cooled to 0° C. Within one hour there were stirred in 410 ml of acetic anhydride and simultaneously 850 ml of 5N sodium hydroxide, whereupon thereafter care was taken that the pH remained in the region of 10-12 and the temperature of +5° C. was not exceeded. After ending the addition stirring was continued for one more hour at 5° C.

The brown solution was treated with concentrated hydrochloric acid until a pH of 1.5 was obtained.

By filtering with suction, washing with water and drying there were obtained 530 grams of acetyl compounds as a pale brown colored powder. This crude product was recrystallized from butanol, whereby there were obtained 335 grams of a colorless mixture of 65% N-acetyl-leucine and 35% N-acetyl-isoleucine.

86.6 grams of this mixture were suspended in 500 ml of water and stirred with 50% aqueous sodium hydroxide until there was obtained a clear solution of pH 7.6. There were added 50 mg of $CoCl_2 \times 6H_2O$ and 5 mg of an aminoacylase from pig kidneys (2000 U/mg). The solution was allowed to stand at 38° C. for 30 hours.

Then the solution formed was cooled to 20° and filtered. There were obtained 24.6 grams of pure L-leucine having a rotary value of $[\alpha]_D^{25} = +15.7°$.

The entire disclosure of German priority application P No. 3318932.3 is hereby incorporated by reference.

What is claimed is:

1. A process of obtaining pure L-leucine from an aminocarboxylic acid mixture containing at least 45 weight percent L-leucine, at most 40 weight percent L-isoleucine and at most 25 weight percent of other aminocarboxylic acids, in each case based on the dry material comprising:
   (a) acetylating the aminoacid mixture,
   (b) precipitating a mixture of N-acetylaminoacids enriched in N-acetyl-L-leucine from the crude mixture of acetylation products,
   (c) subjecting this N-acetyl-L-leucine enriched mixture in aqueous solution having a concentration between 0.1 and 1.5 moles/l of N-acetyl-L-leucine at a pH between 6 and 8 and a temperature between 10° and 40° C. in the presence of an effector of hydrolysis by a L-aminoacid acylase until 30 to 95% of the N-acetyl-L-leucine is hydrolyzed to the free aminoacid, and
   (d) isolating pure L-leucine from the crude hydrolysis mixture.

2. A process according to claim 1 including the step of recrystallizing the mixture of N-acetylamino acids precipitated in step (b) from water, a water miscible aliphatic alcohol having 1 to 4 carbon atoms or a mixture of water and such an alcohol before proceeding with step (c).

3. A process according to claim 2 wherein the effector is the ions $Ca^{2+}$, $Fe^{2+}$, $Mn^{2+}$, $Mg^{2+}$, $Zn^{2+}$, or $Co^{2+}$.

4. A process according to claim 3 wherein the effector is employed as the chloride salt.

5. A process according to claim 4 wherein the salt is $CoCl_2$.

6. A process according to claim 1 wherein the effector is the ions $Ca^{2+}$, $Fe^{2+}$, $Mn^{2+}$, $Mg^{2+}$, $Zn^{2+}$, or $Co^{2+}$.

7. A process according to claim 6 wherein the effector is employed as the chloride salt.

8. A process according to claim 7 wherein the salt is $CoCl_2$.

* * * * *